(12) United States Patent
Guzaev (10) Patent No.: US 7,723,528 B2
(45) Date of Patent: May 25, 2010

(54) SULFUR TRANSFER REAGENTS FOR OLIGONUCLEOTIDE SYNTHESIS

(75) Inventor: Andrei P. Guzaev, Vista, CA (US)

(73) Assignee: AM Chemicals LLC, Oceanside, CA (US)

( * ) Notice: Subject to any disclaimer, the term of this patent is extended or adjusted under 35 U.S.C. 154(b) by 147 days.

(21) Appl. No.: 12/134,136

(22) Filed: Jun. 5, 2008

(65) Prior Publication Data

US 2009/0306358 A1 Dec. 10, 2009

(51) Int. Cl.
*C07D 413/00* (2006.01)
(52) U.S. Cl. .................. 548/123; 548/100; 536/18.5; 536/18.6; 536/18.7; 536/22.1; 536/25.3
(58) Field of Classification Search .............. None
See application file for complete search history.

(56) References Cited

U.S. PATENT DOCUMENTS

| | | | |
|---|---|---|---|
| 5,852,168 | A | 12/1998 | Barany et al. |
| 6,242,591 | B1 | 6/2001 | Cole et al. |
| 6,500,944 | B2 | 12/2002 | Roy et al. |
| 7,098,325 | B2 | 8/2006 | Martin et al. |
| 2005/0182025 | A1 | 8/2005 | Tseng |

FOREIGN PATENT DOCUMENTS

WO WO 97/41130 11/1997

OTHER PUBLICATIONS

Efimov, V.A. et al, New efficient sulfurizing reagents for the preparation of oligodeoxyribonucleotide phosphorothioate analogues, Nucl. Acids Res. 23, 4029-4033 (1995).
Iyer, R.P. et al., The Automated Synthesis of Sulfur-Containing Oligodeoxyribonucleotides Using 3H-1,2-Benzodithiol-3-one 1,1-Dioxide as a Sulfur-Transfer Reagent, J. Org. Chem. 55, 4693-4699 (1990).
Kumar, G. and Poonian, M.S., Improvements in Oligodeoxyribonucleotide Synthesis: Methyl N,N-Dialkylphosphoramidite Dimer Units for Solid Support Phosphite Methodology, J. Org. Chem. 49(25), 4905-12 (1984).
Rao, V. M. et al., Dibenzoyl Tetrasulfide—A Rapid Sulphur Transfer Agent in the Synthesis of Phosphorothioate Analogues of Oligonucleotides, Tetrahedron Lett. 33, 4839-4842 (1992).
Rao, V.M. and Macfarlane, K., Solid Phase Synthesis of Phosphorothioate Oligonucleotides Using Benzyltriethylammonium Tetrathiomolybdate as a Rapid Sulfur Transfer Reagent, Tetrahedron Lett. 35, 6741-6744 (1994).
Song, Q. and Jones, R.A., Use of Silyl Ethers as Fluoride ion Scavengers in RNA Synthesis, *Tetrahedron Lett. 40*, 4653-4654 (1999).
Stec, W.J. et al., Bis(O,O-Diisopropoxy Phosphinothioyl) Disulfide—A Highly Efficient Sulfurizing Reagent for Cost-Effective Synthesis of Oligo(Nucleoside Phosphorothioate)s Tetrahedron Lett. 33, 5317-5320 (1993).
Usman, N. et al., Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethionine tRNA, J. Am. Chem. Soc. 109, 7845-7854 (1987).
Vu, H. and Hirschbein, B.L., Internucleotide Phosphite Sulfurization With Tetraethylthiuram Disulfide. Phosphorothioate Oligonucleotide Synthesis Via Phosphoramidite Chemistry, Tetrahedron Lett. 32, 3005-3008 (1991).
Zhang, Z. et al., Solid Phase Synthesis of Oligonucleotide Phosphorothioate Analogues Using 3-Methyl-1,2,4-dithioazolin-5-one (MEDITH) as a New Sulfur-Transfer Reagent, Tetrahedron Lett. 40, 2095-2098 (1999).
International Search Report dated Nov. 5, 2009 for PCT Application No. PCT/US2009/41569.
Lemaitre et al., Sulfurizing Reagent II and its Use in Synthesizing Oligonucleotide Phosphorothioates, The Glen Report, Supplementary Material, Dec. 2006, vol. 18 No. 1, pp. 1-6.

*Primary Examiner*—Patrick T Lewis
(74) *Attorney, Agent, or Firm*—Foley & Lardner LLP; Stephen E. Reiter (57) ABSTRACT

The use of N-formamidino-5-amino-3H-1,2,4-dithiazole-3-thiones as novel, efficient sulfur-transfer reagents is disclosed. The sulfur transfer from these reagents to compounds containing P(III) atom, triphenylphosphine, 5'-O-DMT-thymidine 2-cyanoethyl-(N,N-diisopropyl)phosphoramidite, and 5'-O-DMT-3'-O-levulinyl dithymidilyl 2-cyanoethyl phosphite, was studied in solution by $^{31}$P NMR and HPLC. The sulfur transfer from title compounds was also studied in the solid-phase synthesis of oligonucleotide phosphorothioates by phosphoramidite methods. In this application, the efficiency of the sulfur transfer reaction for 2'-deoxyoligonucleotides was better than 99.5%. The novel sulfurizing agents are synthesized, at low cost, using simple chemical methods. As opposed to many sulfur transfer reagents known in the prior art such as 1,2-benzodithiol-3-one-1,1-dioxide (Beaucage reagent) and 5-ethoxy-3H-1,2,4-dithiazole-2-one (EDIT), the sulfurizing agents disclosed herein are highly stable in solution, which increases their practical and commercial value.

14 Claims, 9 Drawing Sheets

SEQUENCE LISTING

```
<160> NUMBER OF SEQ ID NOS: 5

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttttttttt                                                          10

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtgagtacc actgattc                                                 18

<210> SEQ ID NO 3
<211> LENGTH: 18
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 2'-O-methyl-u
<220> FEATURE:
<221> NAME/KEY: modified_base
<222> LOCATION: (2)
<223> OTHER INFORMATION: 2'-O-methyl-g
<220> FEATURE:
<221> NAME/KEY: modified_base
<222> LOCATION: (3)
```

```
<223> OTHER INFORMATION: 2'-O-methyl-u
<220> FEATURE:
<221> NAME/KEY: modified_base
<222> LOCATION: (4)
<223> OTHER INFORMATION: 2'-O-methyl-g
<220> FEATURE:
<221> NAME/KEY: modified_base
<222> LOCATION: (5)
<223> OTHER INFORMATION: 2'-O-methyl-a
<220> FEATURE:
<221> NAME/KEY: modified_base
<222> LOCATION: (14)
<223> OTHER INFORMATION: 2'-O-methyl-g
<220> FEATURE:
<221> NAME/KEY: modified_base
<222> LOCATION: (15)
<223> OTHER INFORMATION: 2'-O-methyl-a
<220> FEATURE:
<221> NAME/KEY: modified_base
<222> LOCATION: (16)..(17)
<223> OTHER INFORMATION: 2'-O-methyl-u
<220> FEATURE:
<221> NAME/KEY: modified_base
<222> LOCATION: (18)
<223> OTHER INFORMATION: 2'-O-methyl-c

<400> SEQUENCE: 3
ugugagtacc actgauuc                                                 18

<210> SEQ ID NO 4
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ugugaguacc acugauuc                                                 18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tagtgaagta cactatgatg t                                             21
```

SULFUR TRANSFER REAGENTS FOR OLIGONUCLEOTIDE SYNTHESIS

BACKGROUND OF THE INVENTION

1. Field of the Invention

The invention relates to the chemical synthesis of oligonucleotides and to chemical entities useful in such synthesis. More specifically, the invention relates to sulfur transfer reagents capable of converting P(III) internucleosidic linkages of oligonucleotides to P(V) phosphorothioate linkages in solution or on solid phase.

2. Summary of the Related Art

Oligonucleotides and modified oligonucleotides are molecular tools of indispensable importance for research in molecular biology and for a variety of diagnostic and pharmaceutical applications including the use of siRNA and antisense inhibition of gene expression. Oligonucleotides that contain unnatural internucleoside linkages where one of the nonbridging oxygen atoms of the phosphate group is replaced by a sulfur atom are referred to as oligonucleotide phosphorothioates. Due to their enhanced nucleolytic stability, oligonucleotide phosphorothioates are among the most commonly used analogues. Their widespread use has led to an increasing demand for expeditious, inexpensive, and efficient methods for their preparation.

Synthesis of oligonucleotides is commonly performed on solid phase using well-established protocols employing phosphoramidite or H-phosphonate methods. Briefly, these approaches comprise anchoring the 3'-most nucleoside to a solid support functionalized with amino and/or hydroxyl moieties and subsequently adding the additional nucleotide residues in stepwise fashion. Internucleoside linkages are formed between the 3' functional group of the incoming nucleoside and the 5' hydroxyl group of the 5'-terminal nucleoside of the solid support-bound oligonucleotide. In the phosphoramidite approach, the internucleoside linkage is a protected phosphite moiety, whereas in the H-phosphonate approach, it is an H-phosphonate moiety. To convert these to the sulfur-containing phosphorothioate internucleoside linkage, the phosphite or H-phosphonate moieties are reacted with an appropriate sulfur transfer reagent. In the H-phosphonate approach, this sulfurization is carried out on all of the H-phosphonate linkages in a single step following the completion of oligonucleotide chain assembly, typically using elemental sulfur in a mixture of carbon disulfide and pyridine. In contrast, the phosphoramidite approach allows one to carry out a stepwise sulfurization following each coupling. Currently, the vast majority of oligonucleotides is synthesized using the phosphoramidite approach.

A number of sulfurization agents has been applied to the synthesis of oligonucleotide phosphorothioates. Examples of such agents include 3H-1,2-benzodithiol-3-one-1,1-dioxide, or Beaucage reagent (Iyer et al., J. Org. Chem. 1990, 55, 4693-4699), tetraethylthiuram disulfide (Vu et al., Tetrahedron Lett. 1991, 32, 3005-3008), dibenzoyl tetrasulfide (Rao et al., Tetrahedron Lett. 1992, 33, 4839-4842), bis(O,O-diisopropoxyphosphinothioyl) disulfide (Stec et al., Tetrahedron Lett. 1993, 33, 5317-5320), benzyltriethylammonium tetrathiomolybate (Rao et al., Tetrahedron Lett. 1994, 35, 6741-6744), bis(p-toluenesulfonyl) disulfide (Efimov et al., Nucl. Acids Res. 1995, 23, 4029-4033), 3-ethoxy-1,2,4-dithiazoline-5-one (EDITH) and 1,2-dithiazolidine-3,5-dione (U.S. Pat. No. 5,852,168), 3-amino-1,2,4-dithiazole-5-thione (U.S. Pat. No. 6,096,881), phenylacetyl disulfide (U.S. Pat. No. 6,242,591), 3-methyl-1,2,4-dithiazolin-5-one (Zhang et al., Tetrahedron Lett. 1999, 40, 2095-2098), 3-phenyl-1,2,4-dithiazoline-5-one (U.S. Pat. No. 6,500,944), and 3-amino-1,2,4-dithiazolidine-5-one (US 2004-559782 20040405).

A widely used Beaucage reagent and EDITH are somewhat difficult to synthesize; their hydrolytic stability is rather low. Agents such as tetraethylthiuram disulfide display slow reaction kinetics and thus are less convenient in high-throughput and large scale applications. To date, only Beaucage reagent and TETD are commercially available.

BRIEF DESCRIPTION OF THE INVENTION

The invention provides novel sulfur transfer reagents for the preparation of oligonucleotide phosphorothioates. The sulfur transfer reagents according to the invention are inexpensive in manufacturing, stable in storage, and highly efficient in sulfurization.

In the first aspect, the invention provides novel sulfur transfer reagents having the structure according to Formula I:

wherein:
- $R^1$ and $R^2$ are independently H, an alkyl group, an aryl group, or an aralkyl group, or
- $R^1$, $R^2$ and the N to which they are attached form a ring structure so that $R^1 + R^2 = -(CH_2)_n-$ or $-(CH_2)_n-X-(CH_2)_n-$,
- each n independently varies from 2 to about 20,
- X is O, NR or S, and
- R is an alkyl group, an aryl group, or an aralkyl group.

The term "alkyl group", as used in this application, refers to a hydrocarbon chain having 1 to about 24 carbon atoms and isomeric forms thereof. Presently preferred alkyl groups have in the range of 1 to about 12 carbon atoms, with alkyl groups having in the range of 1 to about 6 carbon atoms being especially preferred. Exemplary alkyl groups include methyl, ethyl, propyl, 1-methylethyl (isopropyl), and butyl.

The term "aryl group", as used in this application, refers to a monovalent aromatic carbocyclic group of from 6 to about 24 carbon atoms, preferably 6 to about 10 carbon atoms. Presently preferred aryl group is phenyl.

The term "aralkyl group", as used in this application, refers to an aryl group that is attached to another moiety via an alkyl linker. Presently preferred aralkyl group is benzyl.

In another aspect, the invention provides novel processes of sulfur transfer that comprise bringing an oligonucleotide having at least one reactive internucleosidic linkage that contains a phosphorous (III) atom in contact with a solution of a sulfur transfer reagent according to Formula I in a suitable organic solvent for a time sufficient for the transfer of sulfur from said reagent to said reactive internucleosidic linkage.

Suitable organic solvents contemplated for use herein can be readily identified by those of skill in the art and include pyridine, tetrahydrofuran, acetonitrile, N,N-dimethylformamide, N,N-dimethylacetamide, and the like, as well as mixtures of any two or more thereof.

In a presently preferred embodiment of the present invention, the oligonucleotide contemplated for use herein is attached to a solid phase material.

DETAILED DESCRIPTION OF THE PREFERRED EMBODIMENTS

The invention relates to the chemical synthesis of oligonucleotides and to chemical entities useful in such synthesis. More specifically, the invention relates to sulfur transfer reagents capable of converting P(III) internucleosidic linkages of oligonucleotides to phosphorothioate linkages in solution or on solid phase. The patents and publications cited in this specification are well-known to those skilled in the art and are hereby incorporated by reference in their entirety.

The invention provides novel sulfur transfer reagents for the preparation of oligonucleotide phosphorothioates and processes for such preparation. The sulfur transfer reagents according to the invention are highly efficient. These compounds are inexpensive to manufacture and are stable in the solid state or in solution over an extensive period of time.

In the first aspect, the invention provides novel sulfur transfer reagents having the structure according to Formula I:

wherein:
R$^1$ and R$^2$ are independently H, an alkyl group, an aryl group, or an aralkyl group, or
R$^1$, R$^2$ and the N to which they are attached from a ring structure so that R$^1$+R$^2$=—(CH$_2$)$_n$— or —(CH$_2$)$_n$—X—(CH$_2$)$_n$—, each n independently varies from 2 to about 20,
X is O, NR or S, and
R is an alkyl group, an aryl group, or an aralkyl group.

In a preferred embodiment of the present invention, R$^1$+R$^2$ for the compound of formula I is —(CH$_2$)$_4$—.

In another preferred embodiment of the present invention, R$^1$+R$^2$ for the compound of formula I is —(CH$_2$)$_2$—O—(CH$_2$)$_2$—.

In yet another preferred embodiment of the present invention, R$^1$ and R$^2$ for the compound of formula I are both C$_2$H$_5$.

In still another preferred embodiment of the present invention, R$^1$ and R$^2$ for the compound of formula I are both n-butyl.

In a further preferred embodiment of the present invention, R$^1$ and R$^2$ for the compound of formula I are both CH$_3$.

In another aspect, the invention provides novel processes of sulfur transfer that comprises bringing an oligonucleotide having at least one reactive internucleosidic linkage that contains a phosphorous (III) atom in contact with a solution of a sulfur transfer reagent according to Formula I in a suitable organic solvent for a time sufficient for the transfer of sulfur from said reagent to said reactive internucleosidic linkage.

Suitable organic solvents contemplated for use herein can be readily identified by those of skill in the art and include pyridine, tetrahydrofuran, acetonitrile, N,N-dimethylformamide, N,N-dimethylacetamide, and the like, as well as mixtures of any two or more thereof.

Sulfur transfer reagents according to the present invention can be dissolved in a suitable organic solvent at a wide range of concentrations, with concentrations typically falling in the range of about 0.001 up to about 1 M.

The ratio of sulfur transfer reagent according to the invention, relative to the oligonucleotide to be reacted therewith can vary widely, typically ranging from about 0.67 up to about 50 equivalents.

Sulfur transfer reagent according to the present invention is typically maintained in contact with oligonucleotide to be reacted therewith for a period of time sufficient to achieve the desired transfer of sulfur thereto, with contact times typically ranging from about 5 seconds up to about 30 minutes.

Preferably, oligonucleotides contemplated for use herein contain 2'-deoxynucleoside, 2'-O-alkylribonucleoside, 2'-O-protected ribonucleoside, LNA nucleoside residues, or the like, or combinations thereof.

Preferably, reactive internucleoside linkages contemplated for modification herein include phosphite, alkylphosphite, thiophosphite, methylphosphonate, H-phosphonate, and H-phosphonothioate internucleosidic linkages.

In a presently preferred embodiment of the present invention, the oligonucleotide contemplated for use herein is attached to a solid phase material.

Exemplary compounds 1-5 may be readily synthesized from commercially available starting materials, as disclosed in Scheme 1.

Scheme 1:

-continued 1-5

1: $R^1 = R^2 = CH_3$;
2: $R^1 = R^2 = C_2H_5$;
3: $R^1 = R^2 = $ n-Butyl;
4: $R^1 + R^2 = $ —(CH$_2$)$_2$—O—(CH$_2$)$_2$—;
5: $R^1 + R^2 = $ —(CH$_2$)$_4$—.

To synthesize compound 1,3-amino-3H-1,2,4-dithiazole-5-thione (TCI America) was dissolved in DMF and treated with dimethylformamide dimethylacetal (Alfa Aesar, Ward Hill, Mass.) at room temperature, followed by precipitation of the product with ethyl ether to give the desired 1 in more than 84% yield and high purity.

Stability and solubility studies of the sulfur transfer reagent 1 were carried out. As disclosed in greater detail below, compound 1 was soluble in mixtures of $CH_3CN$ and pyridine, tetrahydrofuran and pyridine, and pyridine alone to concentrations sufficient for performing their function. Compound 1 was stable in mixtures of $CH_3CN$ and pyridine and pyridine alone for more than 20 weeks. Over the test period, no precipitate was deposited from the solutions. In the functional test, compound 1 did not show any deterioration of the ability to transfer sulfur to solid support-bound internucleosidic phosphite triesters.

Figure 1:
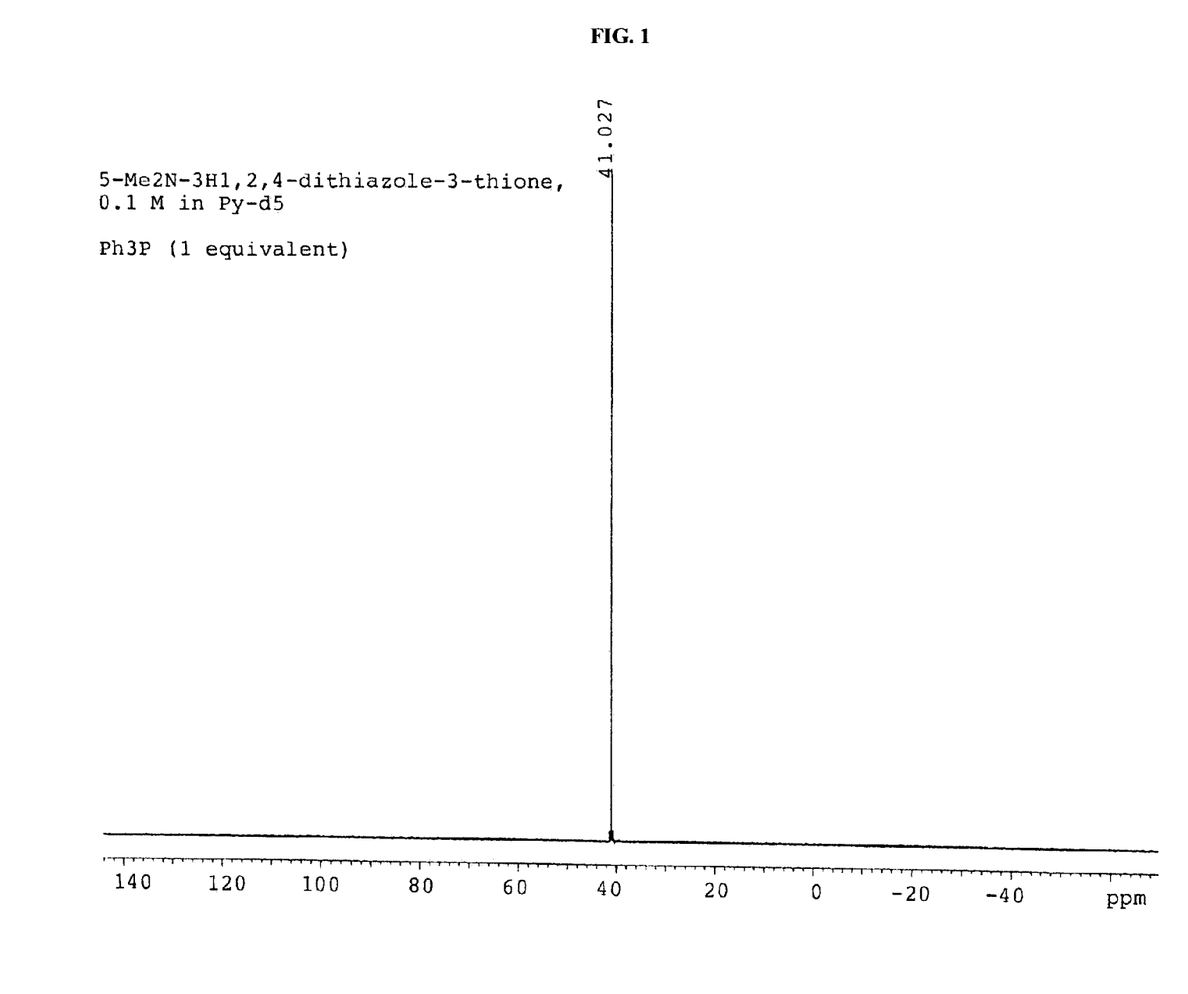
FIG. 1 shows a $^{31}$P NMR spectrum of a mixture formed by equimolecular amounts of compound 1 (see Example 2) and Ph$_3$P.
Figure 3:
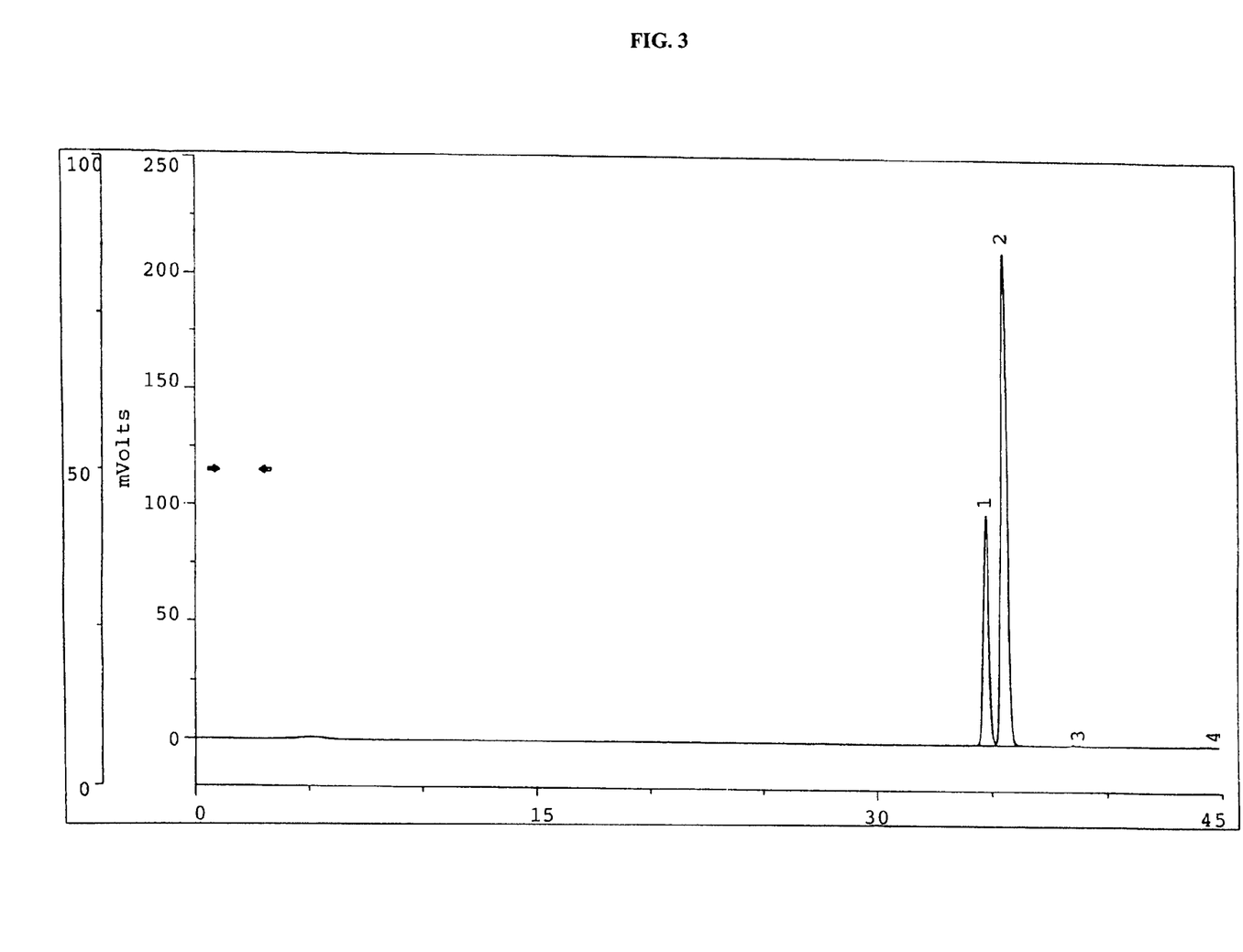
FIG. 3 shows a HPLC profile of a mixture formed by equimolecular amounts of compound 1 and 5'-O-(4,4'-dimethoxytrityl)-3'-O-levulinyl dithymidyl 2-cyanoethyl phosphite (9).

The efficiency of these new sulfur-transfer reagents was first evaluated by mixing equimolecular amounts of 1-5 with triphenylphosphine in pyridine-d5 and monitoring the progress of the reaction by $^{31}P$ NMR (see Scheme 2 and FIGS. 1 and 3).

Scheme 2:

With all of compounds 1-5, the substrate disappeared quantitatively in less than 5 min to give triphenylphosphine sulfide in more than 99% yield plus triphenylphosphine oxide (<0.1%). The stoichiometry of the sulfur transfer was determined by mixing aliquots of 1 with aliquots of triphenylphosphine (1 to 5 equivalents). It was found that two equivalents of compound 1 is capable of producing 3 equivalents of triphenylphosphine sulfide.

Figure 2:
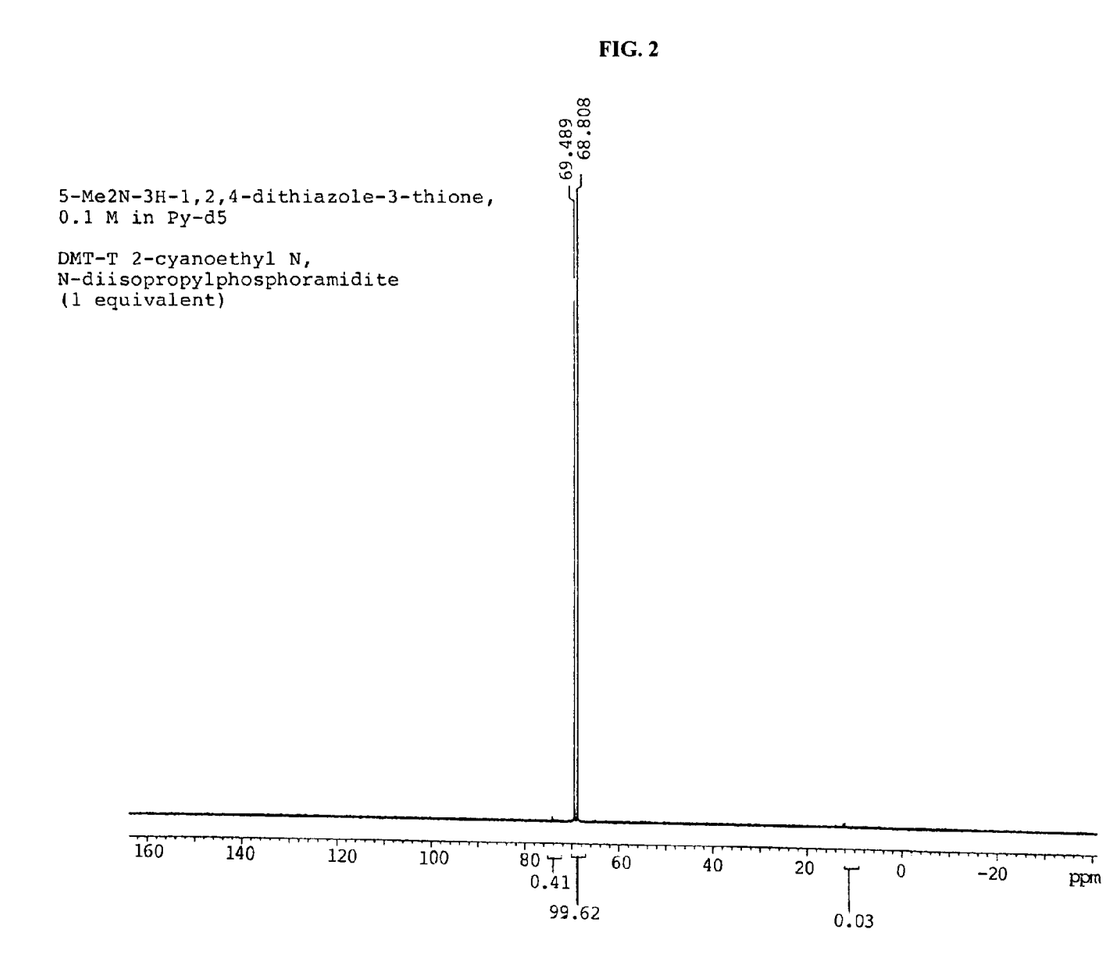
FIG. 2 shows a $^{31}$P NMR spectrum of a mixture formed by equimolecular amounts of compound 1 and 5'-O-(4,4'-dimethoxytrityl)thymidine 2-cyanoethyl-(N,N-diisopropyl) phosphoramidite 6 (see Example 8).

In a similar manner, compound 1 was reacted with an equimolecular amount of 5'-O-(4,4'-dimethoxytrityl)thymidine 2-cyanoethyl 3'-O—(N,N-diisopropyl)phosphoramidite 6 (Scheme 3) to give thionophosphoramidate 7 as a mixture of diastereomers in more than 99.9% yield as judged by $^{31}P$ NMR (FIG. 2).

Scheme 3:

To further evaluate the usefulness of 1 as a sulfur transfer reagent, a protected dithymidilyl monophosphorothioate 11 was synthesized by reacting phosphoramidite 6 with 3'-O-levulinylthymidine 8 in the presence of 1H-tetrazole (Scheme 4).

Scheme 4: Synthesis of compound 10.

Figure 4:
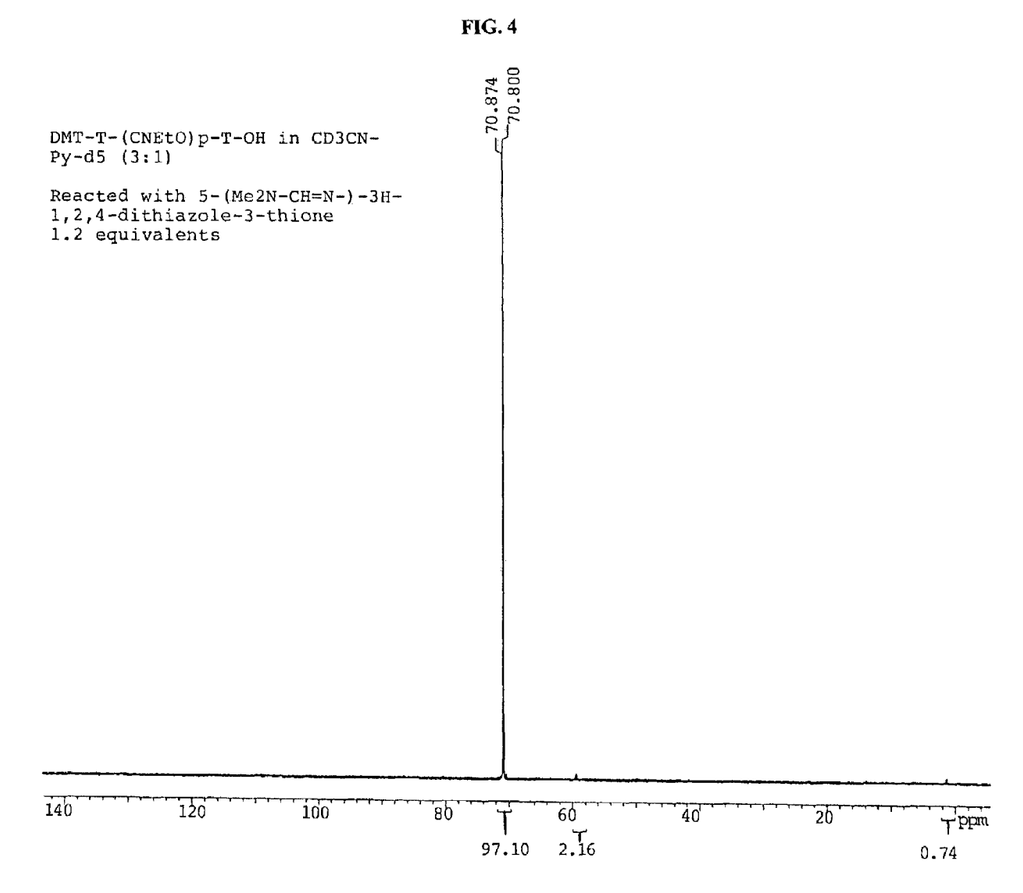
FIG. 4 shows a $^{31}$P NMR spectrum of a mixture formed by equimolecular amounts of compound 1 and 5'-O-(4,4'-dimethoxytrityl)-3'-O-levulinyl dithymidyl 2-cyanoethyl phosphate (9).
Figure 5:
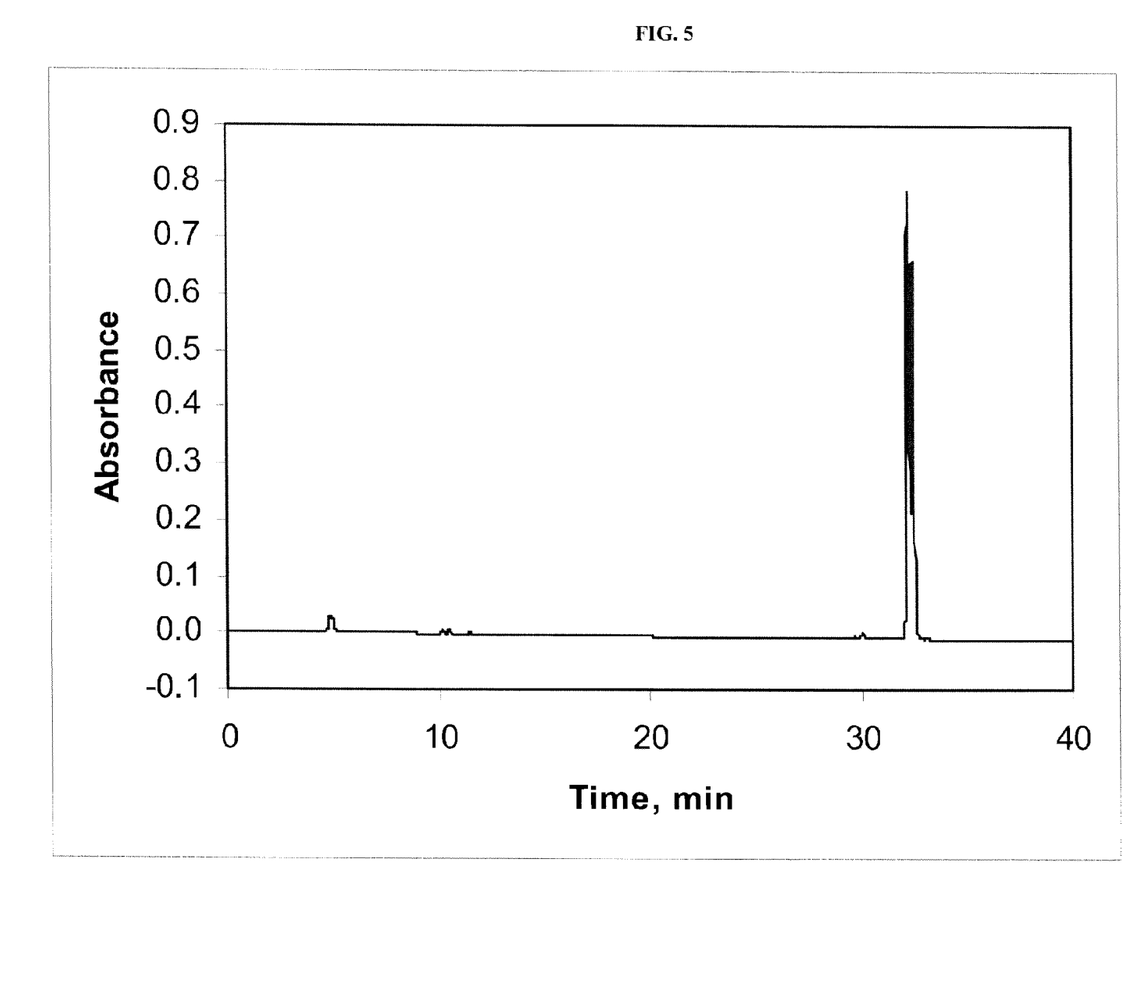
FIG. 5 shows a HPLC profile of crude DMT-T2 phosphorothioate synthesized on solid phase using 1 as a sulfur transfer agent.

Without isolation, the protected phosphite triester 9 was treated with 1.2 molar excess of 1, and 3'-levulinyl protecting group was removed by further treatment with hydrazinium acetate in a mixture of pyridine and acetic acid. Upon aqueous work-up, compound 10 was analyzed by $^{31}$P NMR and reverse-phase HPLC (FIGS. 4 and 5, respectively). The results showed that the efficiency of the sulfur transfer was better than 99.3%.

Finally, the usefulness of compound 1 as an efficient sulfur transfer reagent was evaluated in a solid phase synthesis of oligonucleotides:

DMT-T$_2$ phosphorothioate,
DMT-T$_{10}$ phosphorothioate (SEQ ID NO: 1) and
DMT-d(5'-TGT GAG TAC CAC TGA TTC-3') phosphorothioate (SEQ ID NO:2). The oligonucleotides were synthesized on 0.2 μmol scale using the following standard protocol for chain assembly:

0.02 to 0.05 M solutions of 1 in appropriate mixtures of CH$_3$CN and pyridine, and 0.5, 1, or 2 min sulfurization time in each synthetic cycle.

Under optimized conditions, the complete sulfur transfer using 0.02, 0.05, and 0.1 M solutions of 3 requires contact times of 2, 1, and 0.5 min, respectively.

After the solid-phase-bound material was released and the protecting groups were removed with concentrated aqueous ammonium hydroxide, the crude oligonucleotide phosphorothioates were analyzed by reverse-phase HPLC and ES MS (FIGS. 6-9). The results show that more than 99.5% sulfur transfer efficiency was achieved at each step, and a yield better than 80% has been achieved in these syntheses.

Accordingly, the efficient preparation of oligonucleotide phosphorothioates by phosphoramidite synthesis in solution and on solid phase using compounds 1-8 as sulfur transfer reagents has been demonstrated. Compounds 1-5 can be synthesized, at low cost, using simple chemical methods. As opposed to many sulfur transfer reagents known in the art such as 3H-1,2-benzodithiol-3-one-1,1-dioxide (Beaucage reagent as disclosed in Beaucage, S. L.; Regan, J. B.; Iyer, R. P. Sulfuration of oligonucleotides by benzodithiole analogs. U.S. Pat. Appl. (1990), 35 pp. US 415710 A0) and 5-ethoxy-3H-1,2,4-dithiazole-2-one (EDIT as disclosed in Barany, G.; Musier-Forsyth, K.; Xu, Q.; Chen, L.; Hammer, R. P. Sulfuration of DNA and RNA using disulfide-containing five-membered heterocycles. PCT Int. Appl. (1997), 130 pp. WO 9741130 A2), compounds 1-5 are highly stable in solution, which increases their practical and commercial value.

EXAMPLES

The following examples are intended to further illustrate certain preferred embodiments of the invention and are not intended to be limiting in nature.

Example 1

General Information

N,N-Dimethylformamide dimethylacetal was obtained from Alfa Aesar (Ward Hill, Mass.). 3-Amino-1,2,4-dithiazole-5-thione was purchased from TCI America. DMT-T-CPG, DMTdC-CPG, 5'-DMT-thymidine cyanoethyl phosphoramidite 6, other deoxynucleoside phosphoramidites, Cap A, Cap B, activator, oxidizing and deblock solutions were purchased from Glen Research, (Sterling, Va.). Anhydrous pyridine, CH$_3$CN and CH$_2$Cl$_2$, and all other chemicals were purchased from Aldrich (Milwaukee, Wis.).

Example 2

N'-(3-thioxo-3H-1,2,4-dithiazol-5-yl)-N,N-dimethyl-methanimidamide (1)

Dimethylformamide dimethylacetal (154.2 g, 1.29 mol) was added dropwise to a stirred solution of 5-amino-3H-1,2,4-dithiazole-5-thione (185.2 g, 1.23 mol) in anhydrous DMF (700 mL) over 30 min at 20-25° C. The reaction mixture was stirred at room temperature for 5 h, and ether (600 mL) was slowly added. The precipitate was filtered off, washed on the filter with ether (3×200 mL), and dried in vacuo to give 213.9 g (84.5%) of the title compound 1 as a lemon-yellow crystalline material.

Example 3

N'-(3-thioxo-3H-1,2,4-dithiazol-5-yl)-N,N-diethyl-methanimidamide (2)

Following the procedure disclosed in Example 2, compound 2 was prepared from 3H-1,2,4-dithiazole-5-thione (3.0 g, 20 mol) and diethylformamide dimethylacetal (3.09 g, 21 mmol) in 84% yield.

Example 4

N'-(3-thioxo-3H-1,2,4-dithiazol-5-yl)-N,N-dibutylmethanimidamide (3)

Following the procedure disclosed in Example 2, compound 3 was prepared from 3H-1,2,4-dithiazole-5-thione (3.0 g, 20 mol) and dibutylformamide dimethylacetal (4.27 g, 21 mmol) in 75% yield.

Example 5

N'-(3-thioxo-3H-1,2,4-dithiazol-5-yl)-N-pyrrolidinomethanimidamide (4)

Following the procedure disclosed in Example 2, compound 4 was prepared from 3H-1,2,4-dithiazole-5-thione (3.0 g, 20 mol) and dimethylacetal of, N-formylpyrrolidine (3.19 g, 22 mmol) in 81% yield.

Example 6

N'-(3-thioxo-3H-1,2,4-dithiazol-5-yl)-N-morpholinomethanimidamide (5)

Following the procedure disclosed in Example 2, compound 5 was prepared from 3H-1,2,4-dithiazole-5-thione (3.0 g, 20 mol) and dimethylacetal of N-formylmorpholine (3.55 g, 22 mmol) in 74% yield.

Example 7

Solubility of Compound 1

Solubility of compound 1 in pyridine alone, THF alone, mixtures of MeCN and pyridine and mixtures of pyridine and THF was determined by dissolving an aliquot of the compound in a calculated amount of warm pyridine followed by adding the respective amount of MeCN or THF. The solutions were kept at room temperature for 24 h. Some useful compositions are:

0.1 M in Py;
0.02 M in THF;
Mixtures of Pyridine and MeCN:
0.06 M in Py-MeCN (50:50);
0.05 M in Py-MeCN (40:60);
0.03 M in Py-MeCN (30:70); and
0.02 M in Py-MeCN (20:80);
Mixtures of Pyridine and THF:
0.1 M in Py-THF (40:60); and
0.05 M in Py-MeCN (20:80).

Example 8

Synthesis of Dinucleotide Phosphorothioate Dimer, 5'-O-(4,4'-dimethoxytrityl)dithymidilyl 2-cyanoethyl phosphorothioate (10)

A solution of commercial 2-cyanoethyl 5'-O-(4,4'-dimethoxytrityl)thymidine 3'-O-(4,4'-diisopropyl)phosphoramidite 6 (2.23 g, 3.0 mmol, Glen Research, Sterling, Va.), thymidine-3'-O-levulinate 8 (1.02 g, 3.0 mmol, prepared as disclosed in Kumar, G.; Poonian, M. S. Improvements in oligodeoxyribonucleotide synthesis: methyl N,N-dialkylphosphoramidite dimer units for solid support phosphite methodology. *J. Org. Chem.* 1984, 49(25), 4905-12), and 0.4 M 1H-tetrazole in MeCN (15 mL) was stirred for 45 min. Saturated aqueous NaHCO$_3$ (30 mL) was added, and the mixture was extracted with CH$_2$Cl$_2$ (3×75 mL). The extracts were dried over Na$_2$SO$_4$ and evaporated in vacuo, the residual oil was dried on an oil pump. A portion of the material obtained (2.36 g, 2.40 mmol) was dissolved in pyridine (15 mL) and treated with N'-(3H-1,2,4-dithiazole-3-thione-5-yl)-N,N-dimethylmethanimidamide 1 (0.59 g, 2.88 mmol) at room temperature. The reaction was monitored by $^{31}$P NMR and found to be complete in 10 min.

Acetic acid (1.14 g, 19 mmol) and hydrazine hydrate (380 mg, 7.6 mmol) were added, and the reaction mixture was left overnight. Saturated aqueous NaHCO$_3$ (100 mL) was added, and the mixture was extracted with CH$_2$Cl$_2$ (3×75 mL). The extracts were dried over Na$_2$SO$_4$ and evaporated in vacuo, the residual oil was dried on an oil pump to give 1.74 g (99%) of the crude dinucleotide phosphorothioate. $^{31}$P NMR, ppm (CD$_3$CN-Py-d$_5$): 70.87 (10, Rp-diastereomer, 45.2%); 70.80 (10, Sp-diastereomer, 54.1%); 1.69 (P=O, 0.7%). An aliqute of this mixture was dissolved in 30% aqueous MeCN and analyzed by reverse-phase HPLC. HPLC analysis was carried out on a Waters Exterra C18 column, 3.5 μm (4.6×100 mm) using 0.05 M aqueous NH$_4$OAc as Buffer A, CH$_3$CN as Buffer B, a linear gradient from 30 to 60% B over a period of 30 ml at a flow rate 1.0 mL/min. the Rp and Sp diastereomers of 10 were eluted at retention times 28.6 and 29.12 min. respectively. The P=O dimer (0.4%) was eluted at a retention time of 26.5 min.

Example 9

Synthesis of Dinucleotide Phosphorothioate Dimer, 5'-O-(4,4'-dimethoxytrityl)dithymidilyl phosphorothioate on solid phase DMT-T CPG 500 (1034 g, 87.9 nmol) was detritylated by treating with dichloroacetic acid (3% in DCM) and was washed 3 times with MeCN. The solid support was suspended in a solution of 1H-tetrazole (98.5 g in MeCN (3 L), and DMT-T 2-cyanoethyl phosphoramidite (262.8 g, 351.5 mmol) was added as a solution in MeCN (700 mL). The mixture was stirred for 15 min., and the solid phase was filtered off and washed 3 times with MeCN. The solid phase was then added to a solution of compound 1 (72.2 g, 351.5 mmol) in pyridine (4.4 L), and the suspension obtained was stirred for 10 min. The solid phase was filtered off, washed twice with DMF and 3 times with MeCN and dried in vacuo. An aliquot of the support-bound dimer (2 mmol) was released from the solid phase by treating with conc. aqueous ammonium hydroxide for 2 h at room temperature. The solution obtained was evaporated in vacuo, the residue was dissolved in 30% aqueous MeCN and analyzed by reverse-phase HPLC. HPLC analysis was carried out on a Zorbax 300SB C8 column, 3.5 μm (4.6×150 mm) using 0.1 M aqueous NH$_4$OAc as Buffer A, 80% aqueous CH$_3$CN as Buffer B, and a linear gradient from 0 to 60% B over a period of 40 min at a flow rate of 1.0 mL/min (FIG. 5). The crude deprotection mixture contained 5'-O-(4,4'-dimethoxytrityl)dithymidilyl phosphorothioate and 5'-O-(4,4'-dimethoxytrityl)dithymidilyl phosphate in a ratio of 99.8:0.2.

Example 10

Synthesis of DMT-T$_{10}$ Phosphorothioate
(SEQ ID NO: 1)

Figure 6:
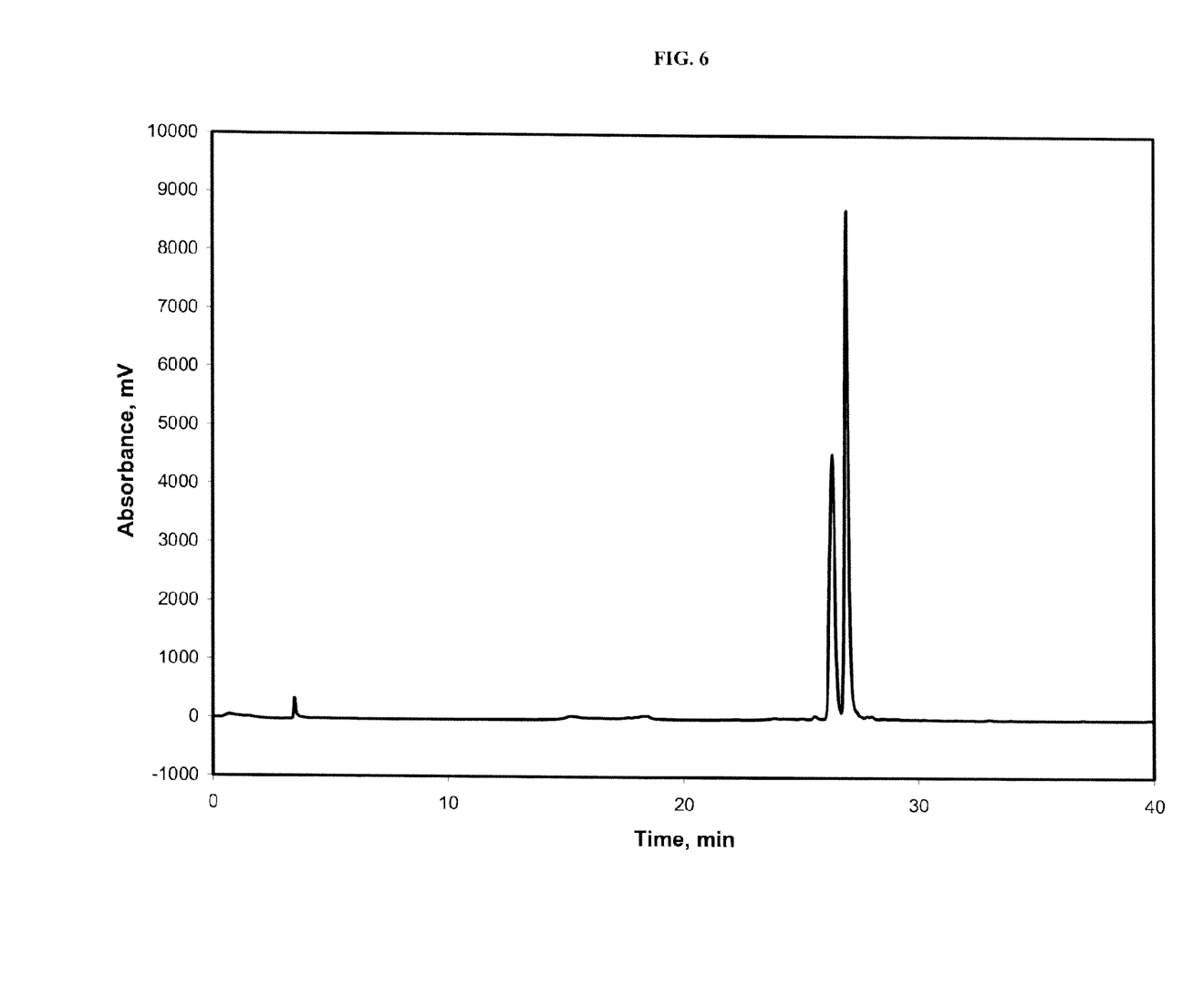
FIG. 6 shows the HPLC of DMT-T$_{10}$ phosphorothioate (SEQ ID NO:1) synthesized using compound 1 as a sulfur transfer agent.

The 2'-deoxyoligonucleotide was assembled on an Applied Biosystems DNA/RNA synthesizer 380B on a 0.2 mmol scale starting with a commercial DMT-dT-Succinyl-CPG (500 A, Glen Research, Sterling, Va.), using 0.1 M solutions of protected nucleoside phosphoramidites (Glen Research, Sterling, Va.), and the following standard protocol of the chain assembly for oligonucleotide phosphorothioates:

Sulfurizing reagent 1 was dissolved in mixtures of pyridine and $CH_3CN$ at 0.02-0.05 M concentration. Sulfurization was carried out by delivering 4 equiv of sulfurizing reagent 1 to columns followed by a waiting period of 1 to 5 min. Under the optimized conditions, the complete sulfur transfer using 0.02, 0.05, and 0.1 M solutions of reagent 1 requires contact times of 2, 1, and 0.5 min, respectively. The final deprotection was carried out by treating the solid supports with concentrated aqueous ammonium hydroxide (2 mL) for 3 h at room temperature. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous $NH_4OAc$ as Buffer A, 80% aqueous $CH_3CN$ as Buffer B, and a linear gradient from 0 to 60% B over a period of 40 min at a flow rate of 1.5 mL/min (FIG. 6). ES MS: 3426.3 (observed), 3426.9 (calculated).

Example 11

Synthesis of DMT-d(TAG TGA AGT ACA CTA TGA TGT) Phosphorothioate (SEQ ID NO: 5)

Figure 7:
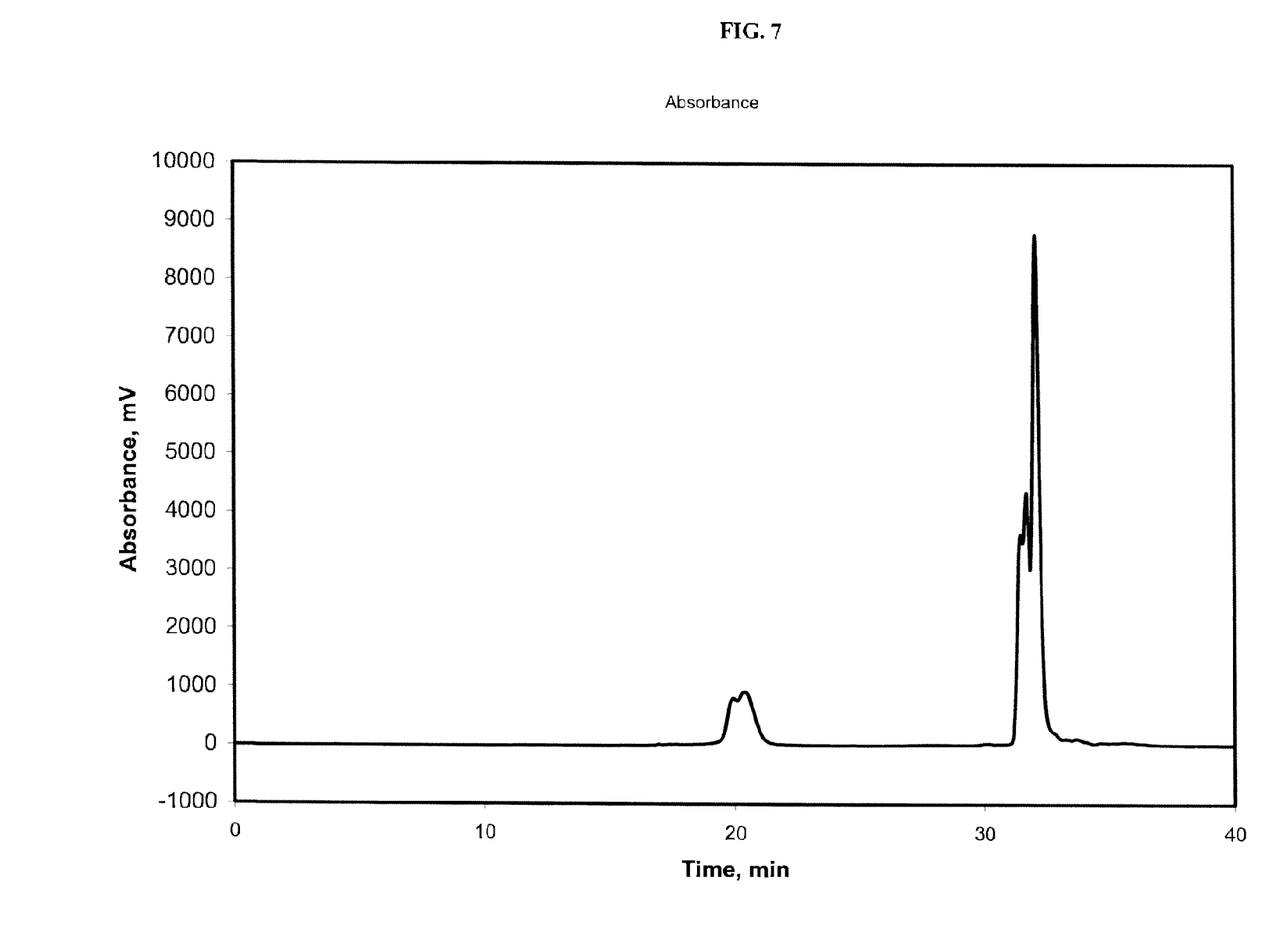
FIG. 7 shows the HPLC of DMT-d(5'-TGT GAG TAC CAC TGA TTC-3') phosphorothioate (SEQ ID NO:2) synthesized using compound 1 as a sulfur transfer agent.
Figure 8:
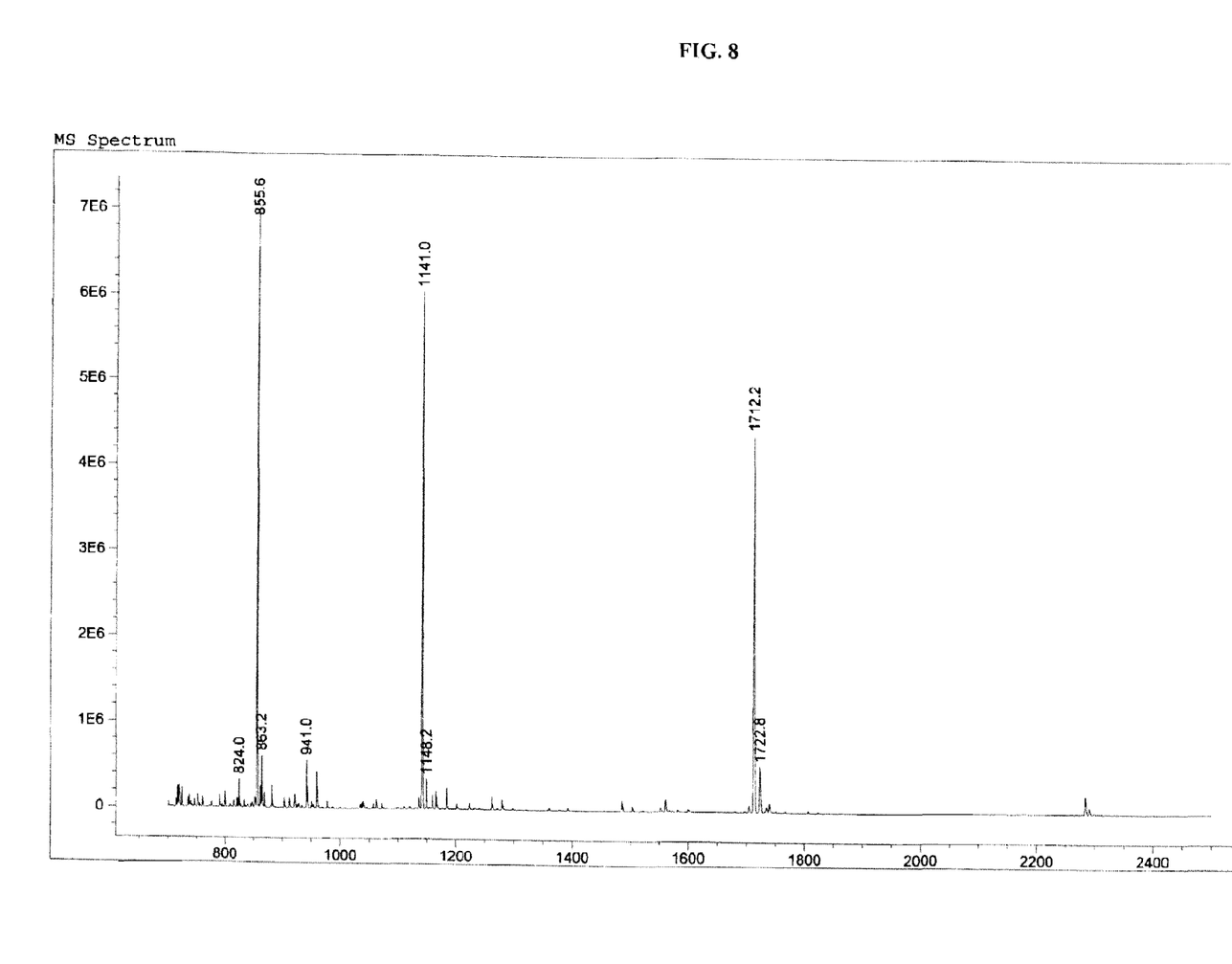
FIG. 8 shows ES MS of DMT-T$_{10}$ phosphorothioate (SEQ ID NO:1) synthesized using compound 1 as a sulfur transfer agent.
Figure 9:
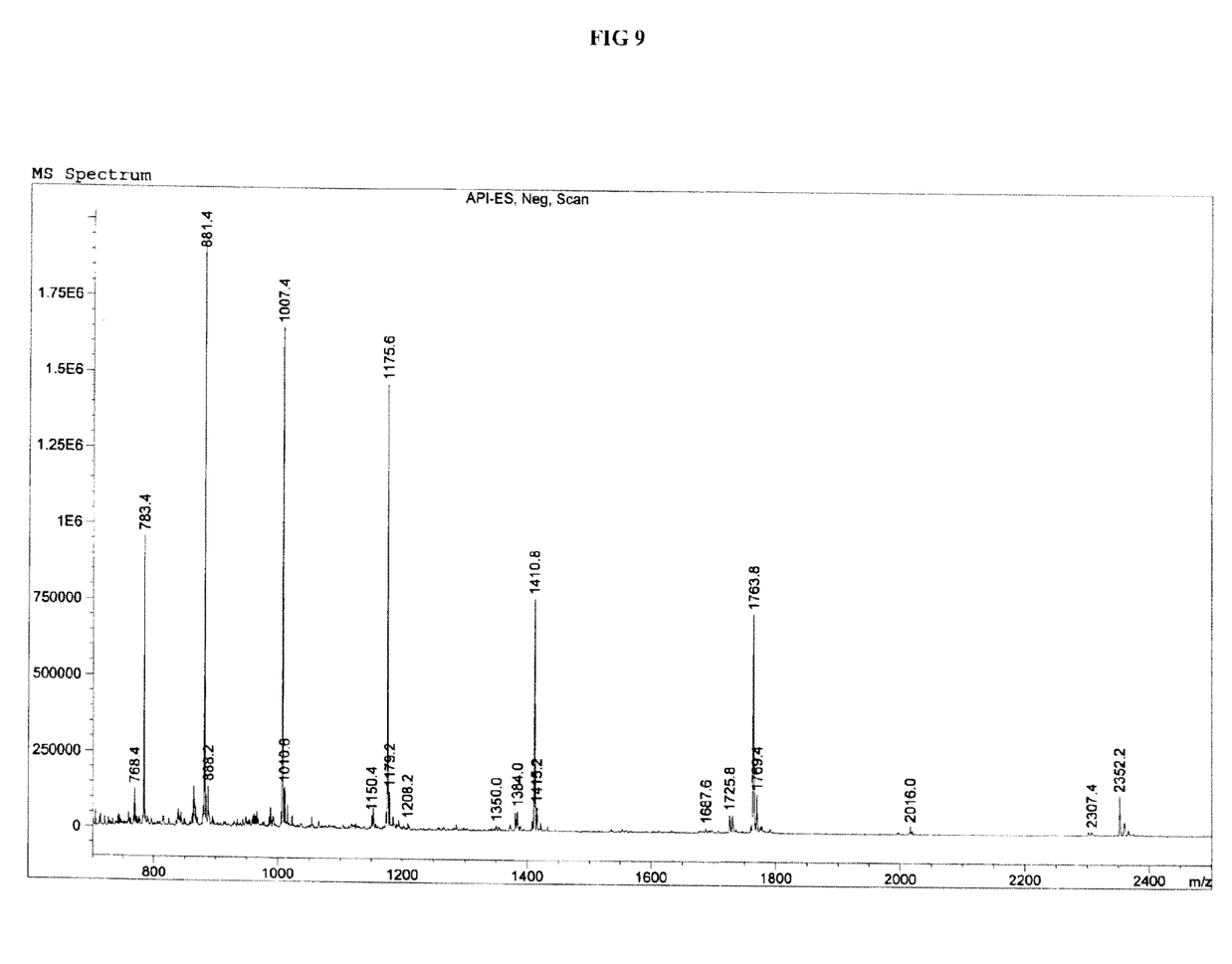
FIG. 9 shows ES MS of DMT-d(5'-TGT GAG TAC CAC TGA TTC-3') phosphorothioate (SEQ ID NO:2) synthesized using compound 1 as a sulfur transfer agent.

The 2'-deoxyoligonucleotide was assembled on an Applied Biosystems DNA/RNA synthesizer 380B on a 0.2 μmol scale starting with a commercial DMT-dT-Succinyl-CPG (500 A, Glen Research, Sterling, Va.), using 0.1 M solutions of protected nucleoside phosphoramidites (Glen Research, Sterling, Va.), and the standard protocol of the chain assembly for oligonucleotide phosphorothioates. Sulfurization was carried out by delivering 4 equiv of a 0.02 M solution of sulfurizing reagent 1 to columns followed by a waiting period for 2 min. The final cleavage and deprotection of nucleic bases was carried out by treating the solid supports with concentrated aqueous ammonium hydroxide (2 mL) at 65° C. for 8 h. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 μM aqueous $NH_4OAc$ as Buffer A, 80% aqueous $CH_3CN$ as Buffer B, and a linear gradient from 0 to 60% B over a period of 40 min at a flow rate of 1.5 mL/min (FIG. 7). ES MS: 7059.2 (observed), 7059.7 (calculated).

Example 12

Synthesis of DMT-($U^{OMe}G^{OMe}U^{OMe}G^{OMe}A^{OMe}G$ TdAdC dCdAdC $TG^{OMe}A^{OMe}U^{OMe}U^{OMe}C^{OMe}$) Phosphorothioate (SEQ ID NO: 3)

Following the procedure described in Example 11, the title oligonucleotide wherein $A^{OMe}$, $G^{OMe}$, $C^{OMe}$, and $U^{OMe}$ refer to the respective 2'-O-methylribonucleotide residues and dA, dG, dC, and T refer to the respective 2'-deoxynucleotide residues, was synthesized. Sulfurizing reagent 1 was dissolved in pyridine at 0.1 M concentration. Sulfurization was carried out by delivering 4 equiv of sulfurizing reagent 1 to columns followed by a waiting period for 5 min. The final cleavage and deprotection of nucleic bases was carried out by treating the solid supports with concentrated aqueous ammonium hydroxide (2 mL) at 65° C. for 8 h. Upon evaporation in vacuo, the crude deprotection mixtures were dissolved in water, filtered, and analyzed by ES MS and reverse-phase HPLC. HPLC analysis was carried out on Waters Delta Pak C18 column, (3.9×300 mm) using 0.1 M aqueous $NH_4OAc$ as Buffer A, 80% aqueous $CH_3CN$ as Buffer B, and a linear gradient from 0 to 60% B over a period of 40 min at a flow rate of 1.5 mL/min. ES MS: 6309.8 (observed), 6309.20 (calculated).

Example 13

Synthesis of UGU GAG UAC CAC UGA UUC Phosphorothioate (SEQ ID NO: 4)

Following the procedure described in Example 11, the title oligonucleotide wherein A, G, C, and U refer to the respective ribonucleotide residues was synthesized using ethylthiotetrazole as an activator. Sulfurizing reagent 1 was dissolved in pyridine at 0.1 M concentration. Sulfurization was carried out by delivering 4 equiv of sulfurizing reagent 1 to columns followed by a waiting period for 3 min. The release from the solid phase and deprotection of nucleic bases were carried out as disclosed in N. Usman, K. K. Ogilvie, M.-Y. Jiang, and R. J. Cedergren, J. Am. Chem. Soc. 1987, 109, 7845-7854, which is incorporated by reference herein in its entirety. The removal of 2'-O-tBDMS groups was carried out as disclosed in Q. Song, R. A. Jones. Use of silyl ethers as fluoride ion scavengers in RNA synthesis. *Tetrahedron Lett.* 1999, 40, 4653-4654, which is incorporated by reference herein in its entirety. The crude deprotection mixture was analyzed by ES MS and ion-exchange HPLC. HPLC analysis was carried out on a Dionex DNAPac PA200 column (4×250 mm) using 0.1 M aqueous Na phosphate, pH 8.5 as Buffer A,). 1 M aqueous Na phosphate plus 1 M NaBr, pH 8.5 as Buffer B, and a linear gradient from 0 to 60% B over a period of 40 min at a flow rate of 1.5 mL/min. ES MS: 5965.9 (observed), 5966.5 (calculated).

Example 14

Stability of N'-(3-thioxo-3H-1,2,4-dithiazol-5-yl)-N, N-dimethylmethanimidamide 1 in solution Stability studies were carried out by keeping a 0.02 M solution of compound 1 in anhydrous pyridine-$CH_3CN$ (20:80) at 25° C. Every two weeks, the solution was used as the sulfurizing reagent in the preparation of DMT-T10 phosphorothioate (SEQ ID NO: 1). Upon completion of the synthesis, the solid phase-bound material was released with concentrated aqueous ammonium hydroxide for 2 h, the solution was evaporated, and the crude oligonucleotide obtained was re-dissolved in water and analyzed by reverse-phase HPLC (FIG. 6). Comparison of the HPLC traces showed no deterioration of the activity of the reagent over a period of 20 weeks, at which point the experiment was terminated.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A sulfur transfer reagent having the general structure according to Formula I:

Formula I:

wherein:

R$^1$ and R$^2$ are independently H, an alkyl group, an aryl group, or an aralkyl group, or R$^1$, R$^2$ and the N to which they are attached form a ring structure so that R$^1$+R$^2$=—(CH$_2$—)$_n$— or —(CH$_2$)$_n$—X—(CH$_2$)$_n$—, each n independently varies from 2 to about 20, X is O, NR or S, and R is an alkyl group, an aryl group, or an aralkyl group.

2. The reagent of claim 1 where R$^1$=R$^2$=CH$_3$.

3. The reagent of claim 1 where R$^1$=R$^2$=C$_2$H$_3$.

4. The reagent of claim 1 where R$^1$=R$^2$=n-butyl.

5. The reagent of claim 1 where R$^1$+R$^2$=—(CH$_2$)$_2$—O—(CH$_2$)$_2$—.

6. The reagent of claim 1 where R$^1$+R$^2$=—(CH$_2$)$_4$—.

7. A process of sulfur transfer that comprises bringing an oligonucleotide having at least one reactive internucleosidic linkage that contains a phosphorous (III) atom in contact with a sulfur transfer reagent according to claim 1 for a time sufficient for the transfer of sulfur from said reagent to said reactive internucleosidic linkage.

8. The process according to claim 7, wherein said oligonucleotide contains 2'-deoxynucleoside, 2'-O-alkylribonucleoside, 2'-O-protected ribonucleoside, LNA nucleoside residues, or combinations of any two or more thereof.

9. The process according to claim 7, wherein said reactive internucleoside linkage is a phosphite, alkylphosphite, thiophosphite, methylphosphonate, H-phosphonate, or H-phosphonothioate internucleosidic linkage.

10. The process according to claim 7 wherein said oligonucleotide is attached to a solid phase material.

11. A process of sulfur transfer that comprises bringing an oligonucleotide having at least one reactive internucleosidic linkage that contains a phosphorous (III) atom in contact with a sulfur transfer reagent according to claim 2 for a time sufficient for the transfer of sulfur from said reagent to said reactive internucleosidic linkage.

12. The process according to claim 11, wherein said oligonucleotide consists of 2'-deoxynucleoside, 2'-O-alkylribonucleoside, 2'-O-protected ribonucleoside, LNA nucleoside residues, or their combinations.

13. The process according to claim 11, wherein said reactive internucleoside linkage is a phosphite, alkylphosphite, thiophosphite, methylphosphonate, H-phosphonate, or H-phosphonothioate internucleosidic linkage.

14. The process according to claim 11 wherein said oligonucleotide is attached to a solid phase material.

* * * * *